(12) United States Patent
Nozulak

(10) Patent No.: US 6,780,861 B2
(45) Date of Patent: Aug. 24, 2004

(54) AZABICYCLIC CARBAMATES AND THEIR USE AS α-7 NICOTINIC ACETYLCHOLINE RECEPTOR AGONISTS

(75) Inventor: Joachim Nozulak, Heitersheim (DE)

(73) Assignee: Novartis AG, Basel (CH)

( * ) Notice: Subject to any disclaimer, the term of this patent is extended or adjusted under 35 U.S.C. 154(b) by 4 days.

(21) Appl. No.: 10/258,920

(22) PCT Filed: May 3, 2001

(86) PCT No.: PCT/EP01/05008
§ 371 (c)(1),
(2), (4) Date: Oct. 31, 2002

(87) PCT Pub. No.: WO01/85727
PCT Pub. Date: Nov. 15, 2001

(65) Prior Publication Data
US 2003/0166654 A1 Sep. 4, 2003

(30) Foreign Application Priority Data
May 5, 2000 (GB) .............................. 0010955

(51) Int. Cl.⁷ ...................... A61K 31/495; A61K 31/44; C07D 241/02; C07D 453/02
(52) U.S. Cl. ...................... 514/249; 514/305; 544/353; 546/133
(58) Field of Search ............................... 514/302, 249; 546/133; 544/353

(56) References Cited

U.S. PATENT DOCUMENTS

| | | | |
|---|---|---|---|
| 5,998,429 A | | 12/1999 | Macor et al. |
| 6,313,247 B1 | * | 11/2001 | Lindner et al. ............. 526/259 |
| 6,479,510 B2 | * | 11/2002 | Myers et al. ................ 514/305 |
| 6,525,065 B1 | * | 2/2003 | Caldwell et al. ............. 514/305 |
| 6,555,552 B2 | * | 4/2003 | Kulagowski et al. ........ 514/304 |
| 6,599,917 B1 | * | 7/2003 | Okada et al. ................ 514/305 |
| 6,624,173 B1 | * | 9/2003 | Crooks et al. .............. 514/305 |

FOREIGN PATENT DOCUMENTS

| | | |
|---|---|---|
| EP | 478 328 A1 | 4/1992 |
| WO | WO 96/08468 | 3/1996 |
| WO | WO 97/21678 | 6/1997 |

* cited by examiner

Primary Examiner—Deborah C Lambkin
(74) Attorney, Agent, or Firm—Joseph J. Borovian; E. Jay Wilusz

(57) ABSTRACT

The invention provides compounds of formula (I) wherein n, A, $R_1$, $R_2$ and $R_3$ are as defined in the description, and the preparation thereof. The compounds of formula (I) are useful as pharmaceuticals.

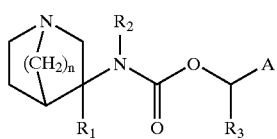

(I)

8 Claims, No Drawings

AZABICYCLIC CARBAMATES AND THEIR USE AS α-7 NICOTINIC ACETYLCHOLINE RECEPTOR AGONISTS

The present invention relates to novel azabicyclic carbamates, their preparation, their use as pharmaceuticals and pharmaceutical compositions containing them.

More particularly the invention provides a compound of formula I

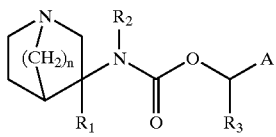

I wherein n is 1 or 2, $R_1$, $R_2$ and $R_3$, independently, are hydrogen or $(C_{1-4})$alkyl and A is a group of formula

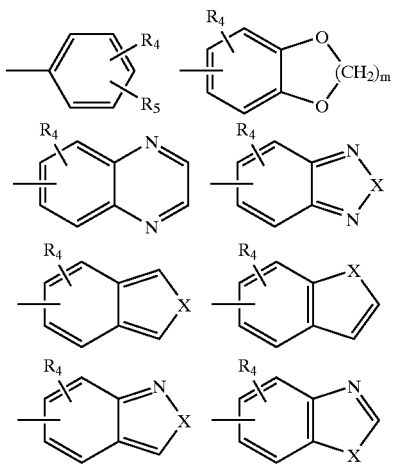

wherein m is 1, 2 or 3, X is O, S, NH or $CH_2$ and $R_4$ and $R_5$, independently, are hydrogen, halogen, hydroxy, $(C_{1-4})$alkyl, $(C_{1-4})$alkoxy, $(C_{1-4})$alkylthio, $(C_{1-4})$alkylamino, nitro, trifluoromethyl or phenyl, in free base or acid addition salt form.

Halogen denotes fluorine, bromine, chlorine or iodine.

Any alkyl, alkoxy and alkylthio groups are branched or straight chain groups. They are preferably methyl, methoxy or methylthio groups.

On account of the asymmetrical carbon atom(s) present in the compounds of formula I and their salts, the compounds may exist in optically active form or in form of mixtures of optical isomers, e.g. in form of racemic mixtures. All optical isomers and their mixtures including the racemic mixtures are part of the present invention.

In a further aspect, the invention provides a process for the production of the compounds of formula I and their salts, comprising the step of reacting a compound of formula II

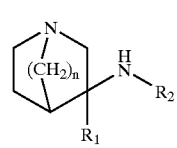

II wherein n, $R_1$ and $R_2$ are as defined above, with a compound of formula III

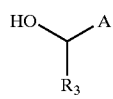

III wherein $R_3$ and A are as defined above, and N,N'-carbonyldiimidazole or di(N-succinimidyl)carbonate, and recovering the resulting compound of formula I in free base or acid addition salt form.

According to a preferred embodiment, in a first step the compound of formula III is reacted with N,N'-carbonyldiimidazole, and the resulting compound is reacted with the compound of formula II.

Alternatively, the compound of formula II can be reacted with a compound of formula IV

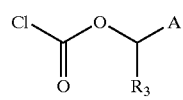

IV wherein $R_3$ and A are as defined above.

The reactions can be effected according to conventional methods, e.g. as described in the examples.

Working up the reaction mixtures according to the above processes and purification of the compounds thus obtained may be carried out in accordance to known procedures.

Acid addition salts may be produced from the free bases in known manner, and vice versa.

Compounds of formula I in optically pure form can be obtained from the corresponding racemates according to well-known procedures. Alternatively, optically pure starting materials can be used.

The starting materials of formula II, III and IV are known or may be obtained from known compounds, using conventional procedures.

Compounds of formula I and their pharmaceutically acceptable acid addition salts, hereinafter referred to as agents of the invention, exhibit valuable pharmacological properties when tested in vitro and in animals, and are therefore useful as pharmaceuticals.

In particular, the agents of the invention are α7 nicotinic acetylcholine receptor (nAChR) agonists.

In functional assays, the agents of the invention display high affinity at the α7 nAChR as shown in the following tests:

a) A functional assay for affinity at human α7 nAChR is carried out with a rat pituitary cell line stably expressing the human α7 nAChR. As a read out, the calcium influx upon stimulation of the receptor is used. In this assay, agents of the invention exhibit $pEC_{50}$ values of about 5 to about 8.

b) To assess the activity of the agents of the invention on the human neuronal nAChR α4β2, a similar functional assay is carried out using a human epithelial cell line stable expressing the human α4β2 subtype. In this assay, agents of the invention show selectivity for the α7 nAChR subtypes.

c) To assess the activity of the compounds of the invention on the "ganglionic subtype" and the muscle type of nicotinic receptor, similar functional assays as described under a) are carried out with a human epithelial cell line stably expressing the human ganglionic subtype or a cell line endogenously expressing the human muscle type of nicotinic receptors. In these assays, agents of the invention display no or little activity on the ganglionic and muscle type of nicotinic receptor subtypes.

In the model of mice showing sensory gating deficit (DBA/2-mice) described by S. Leonard et al. in Schizophrenia Bulletin 22, 431–445 (1996), the agents of the invention induce significant sensory gating at concentrations of about 10 to about 40 µM.

The agents of the invention are therefore useful for the treatment of psychotic disorders such as schizophrenia, mania, depression and anxiety, and for the treatment of neurodegenerative disorders such as senile dementia, Alzheimer's disease and other intellectual impairment disorders, such as attention deficit hyperactivity disorders (ADHD); Parkinson's disease, Huntington's chorea, amyotrophic lateral sclerosis and multiple sclerosis. The usefulness of α7 nAChR agonists in neurodegeneration is documented in the literature, e.g. in Wang et al., J. biol. Chem. 275, 5626–5632 (2000).

For the above-mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.01 to about 100, preferably from about 0.1 to about 50 mg/kg animal body weight. In larger mammals, for example humans, an indicated daily dosage is in the range from about 1 to about 500, preferably from about 5 to about 300 mg of an agent of the invention conveniently administered, for example, in divided doses up to four times a day or in sustained release form.

The agent of the invention may be administered by any conventional route, in particular enterally, preferably orally, for example in the form of tablets or capsules, or parenterally, for example in the form of injectable solutions or suspensions.

The preferred compound is the stereoisomer of the (1-aza-bicyclo[2.2.2]oct-3-yl)-carbamic acid 1-(2-fluorophenyl)-ethyl ester, the succinate of which has a melting point of 83–84° C. and which has an optical rotation of +14.6° (c=1; water, 20° C., 589 nm), which is the compound of Example 61.

In accordance with the foregoing, the present invention also provides an agent of the invention, for use as a pharmaceutical, e.g. for the treatment of any condition mentioned above.

The present invention furthermore provides a pharmaceutical composition comprising an agent of the invention in association with at least one pharmaceutical carrier or diluent. Such compositions may be manufactured in conventional manner. Unit dosage forms contain, for example, from about 0.25 to about 150, preferably from about 1 to about 25 mg of a compound according to the invention.

Moreover the present invention provides the use of an agent of the invention, for the manufacture of a medicament for the treatment of any condition mentioned above.

In still a further aspect the present invention provides a method for the treatment of any condition mentioned above, in a subject in need of such treatment, which comprises administering to such subject a therapeutically effective amount of an agent of the invention.

The following examples illustrate the invention.

EXAMPLE 1

(1-Aza-bicyclo[2.2.2]oct-3-yl)-carbamic acid 1-phenyl-ethyl ester

Imidazole-1-carboxylic acid 1-phenyl-ethyl ester

To a solution of DL-1-phenylethanol 1.21 ml (10.0 mmol) in 10 ml tetrahydrofurane, N,N'-carbonyldiimidazole 1.70 g (10.5 mmol) is added. The white suspension is heated up to 50° C. and stirred for 40 minutes at this temperature. The reaction mixture is cooled and evaporated. The crude product is purified by flash chromatography (hexane/ethyl acetate 80/20) to yield the title product as colorless oil.

(1-Aza-bicyclo[2.2.2]oct-3-yl)-carbamic acid 1-phenyl-ethyl ester

To a solution of imidazole-1-carboxylic acid 1-phenyl-ethyl ester 0.50 g (2.31 mmol) in 5 ml dimethylformamide, 3-aminoquinuclidine dihydrochloride 0.46 g (2.31 mmol) and sodium carbonate 0.49 g (4.62 mmol) are added. The suspension is heated up to 80° C. and stirred for 18 hours at this temperature. The reaction mixture is then cooled and extracted with water and ethylacetate. The combined organic phases are dried and evaporated. The oily residue is dried, dissolved in ether and acidified with a 4 M hydrochloric acid dioxane solution. The precipitating crystals are filtered, washed with ether and dried to give the title product. Mp=71–72° C. (decomposition).

EXAMPLE 2

(1-Aza-bicyclo[2.2.2]oct-3-yl)-carbamic acid benzyl ester

3-Aminoquinuclidine dihydrochloride 996 mg (5.0 mmol) is added slowly to a stirred suspension of 676 mg (15.5 mmol) sodium hydride (dispersion 55%) in dimethylformamide (15 ml). Thereafter the suspension is stirred for another 90 minutes at room temperature and then carbobenzoxy chloride 0.72 ml (5.1 mmol) is added slowly. After another two hours at room temperature, the suspension is quenched by carefully adding water. The solvent is then evaporated at 70° C./16 mbar. The residue is taken up in water and ethyl acetate. The organic phase is separated and the water phase two-times re-extracted with ethyl acetate. The combined organic phase is dried and evaporated to give the crude oily product which is taken up in dioxane and 0.72 ml of a 4M hydrochloric acid is added. The precipitating product is recrystallised from dioxane/ether to give the hydrochloride of the title product. Mp=192–193° C.

EXAMPLE 3

(R)-(+)-(1-Aza-bicyclo[2.2.2]oct-3-yl)-carbamic acid benzyl ester

Sodium hydride (dispersion 55%) 0.33 g (7.5 mmol) is washed with petrolether and the solvent is removed by separation (decantation). Then, the sodium hydride is carefully suspended in dimethylformamide (12.5 ml). To this suspension (R)-(+)-3-aminoquinuclidine dihydrochloride 0.50 g (2.5 mmol) is added. The initially exothermic reaction is then stirred at room temperature for one hour and then carbobenzoxy chloride 0.39 ml (2.75 mmol) is added to the reaction mixture within 15 minutes. The again initially exothermic reaction is stirred at room temperature for 90 minutes, then the mixture is poured into 10% brine (NaCl/water solution) and then four-times extracted with toluene. The combined organic phases are dried and evaporated. The crude oily residue is dissolved in dioxane (5 ml) and 0.31 ml of a 4 M hydrochloric acid is added. The mixture is then stirred at room temperature till the product precipitates. The crystals are filtered, washed with dioxane and ether and dried to give the title product. Mp=228–229° C. Optical rotation +6.3° (c=0.5, water).

EXAMPLE 4

(S)-(−)-(1-Aza-bicyclo[2.2.2]oct-3-yl)-carbamic acid benzyl ester

Sodium hydride (dispersion 55%) 0.33 g (7.5 mmol) is washed with petrolether and the solvent is removed by separation (decantation). Then, the sodium hydride is carefully suspended in dimethylformamide (12.5 ml). To this suspension (S)-(−)-3-aminoquinuclidine dihydrochloride 0.50 g (2.5 mmol) is added. The initially exothermic reaction is then stirred at room temperature for one hour and then carbobenzoxy chloride 0.39 ml (2.75 mmol) is added to the reaction mixture within 15 minutes. The again initially exothermic reaction is stirred at room temperature for 90 minutes then the mixture is poured into 10% brine (NaCl/water solution) and then four-times extracted with toluene. The combined organic phases are dried and evaporated. The crude oily residue is dissolved in dioxane (5 ml) and 0.31 ml of a 4 M hydrochloric acid is added. The mixture is then stirred at room temperature till the product precipitates. The crystals are filtered, washed with dioxane and ether and dried to give the title product. Mp=221–223° C. Optical rotation −8.0° (c=0.5, water).

EXAMPLE 5

(1-Aza-bicyclo[2.2.2]oct-3-yl)-carbamic acid 4-butyl-benzyl ester

Triethylamine 1.05 ml (7.5 mmol) and 0.80 g di-(N-succinimidyl)carbonate are added to a solution of (4-butyl-phenyl)methanol 0.47 ml (2.75 mmol) in 15 ml dichloromethane. The initial suspension is stirred at room temperature for 45 minutes to become a clear solution. This mixture is added dropwise to a solution of 3-aminoquinuclidine 0.32 g (2.5 mmol) and 0.52 ml (1.5 mmol) triethylamine in 10 ml dichloromethane. The reaction mixture is subsequently stirred for another two hours at room temperature. Afterwards the mixture is washed with 20 ml water. The organic phase is separated, dried and evaporated. The crude product is dissolved in 5 ml dichloromethane and acidified with a saturated solution of hydrochloric acid in ether. By addition of 50 ml ether a white product precipitates. The crystals are filtered, washed with ether and dried to give the title product. Mp=174–175° C. decomposition).

The following compounds of formula I wherein n is 2, $R_1$ and $R_2$ are hydrogen and A is a substituted phenyl group can be prepared in analogy to Examples 1, 2 or 5.

| Example | $R_3$ | $R_4$ | $R_5$ | Mp/Optical Rotation |
|---|---|---|---|---|
| 6 | H | o-OMe | H | 89–90° C. (hydrochloride) |
| 7 | H | 2-OMe | 3-OMe | 93–95° C. (hydrochloride) |
| 8 | H | p-phenyl | H | 193–195° C. (hydrochloride) |
| 9 | H | o-Br | H | 203–204° C. (hydrochloride) |
| 10 | H | o-NO$_2$ | H | 177–178° C. (hydrochloride) |
| 11 | H | p-NO$_2$ | H | 89–90° C. (hydrochloride) |
| 12 | H | 2-OMe | 5-Br | 147–149° C. (hydrochloride) |
| 13 | H | m-phenoxy | H | 82–83° C. (hydrochloride) |
| 14 | H | o-Cl | H | 82–83° C. (hydrochloride) |
| 15 | H | 3-NO$_2$ | 5-NO$_2$ | 93–94° C. (hydrochloride) |
| 16 | H | 3-Cl | 4-Cl | * |
| 17 | H | m-OMe | H | 139–140° C. (hydrochloride) |
| 18 | H | 3-NO$_2$ | 4-Me | 86–88° C. (hydrochloride) |
| 19 | H | 3-Me | 5-Me | 183–184° C. (hydrochloride) |
| 20 | H | p-CF$_3$ | H | 143–144° C. (hydrochloride) |
| 21 | H | o-Me | H | 174–176° C. (hydrochloride) |
| 22 | H | p-Me | H | 194–196° C. (hydrochloride) |
| 23 | H | p-isopropyl | H | 235° C. (hydrochloride) |
| 24 | Me | p-Me | H | 168–170° C. (hydrochloride) |
| 25 cis/trans racemic mixture | Me | H | H | 71–72° C. (hydrochloride) |
| 26 Stereoisomer-1 | Me | H | H | 182–184° C. (hydrochloride); optical rotation: +32.4° (c = 1; water 24° C., 589 nm) |
| 27 Stereoisomer-2 | Me | H | H | 151–152° C. (succinate) optical rotation: −9.7° (c = 1; methanol, 22° C., 589 nm) |
| 28 Stereoisomer-3 | Me | H | H | optical rotation: +12.5° (c = 1; methanol, 20° C., 589 nm) |
| 29 Stereoisomer-4 | Me | H | H | 117–119° C. (fumarate) optical rotation: −25.0° (c = 1; methanol, 20° C., 589 nm) |
| 30 | H | 3-OMe | 5-OMe | 179–180° C. (hydrochloride) |
| 31 | H | 3-Me | 4-NO$_2$ | 165–167° C. (hydrochloride) |
| 32 | Me | 2-Cl | 4-Cl | 212–214° C. (hydrochloride) |
| 33 | H | p-Ethyl | H | 208–209° C. (hydrochloride) |
| 34 | H | p-Br | H | 190–191° C. (hydrochloride) |
| 35 | H | 3-CF$_3$ | 5-CF$_3$ | 157–158° C. (hydrochloride) |
| 36 | H | p-SMe | H | 164–166° C. (hydrochloride) |
| 37 | H | 2-NO$_2$ | 5-Me | 198–199° C. (hydrochloride) |
| 38 | H | 3-OMe | 4-OMe | 221–223° C. (hydrochloride) |
| 39 | H | 2-Cl | 6-Cl | 251–252° C. (hydrochloride) |
| 40 | H | p-CO$_2$Me | H | 220–222° C. (hydrochloride) |
| 41 | Me | p-tButyl | H | 232–233° C. (hydrochloride) |
| 42 | Ethyl | H | H | ** |
| 43 | Me | p-Cl | H | 132–135° C. (hydrochloride) |
| 44 | Me | o-Me | H | 219–220° C. (hydrochloride) |
| 45 | Me | p-Br | H | 163–165° C. (hydrochloride) |
| 46 | Me | 3-Cl | 4-Cl | 240–241° C. (hydrochloride) |
| 47 | Me | p-F | H | 219–220° C. (hydrochloride) |
| 48 | H | m-Br | H | 186–187° C. (hydrochloride) |
| 49 | H | m-Me | H | 174–175° C. (hydrochloride) |
| 50 | H | m-OBenzyl | H | 168–169° C. (hydrochloride) |
| 51 | H | 2-Cl | 5-Cl | 205–207° C. (hydrochloride) |
| 52 | H | 2-OMe | 5-OMe | 162–163° C. (hydrochloride) |
| 53 | H | 2-NO$_2$ | 4-Cl | 204–205° C. (hydrochloride) |
| 54 cis/trans racemic mixture | Me | o-Cl | H | 230–232° C. (hydrochloride) |
| 55 Stereoisomer-1 | Me | o-Cl | H | 229-230° C. (hydrochloride) optical rotation: −8.6° (c = 1; water, 20° C., 589 nm) |
| 56 Stereoisomer-2 | Me | o-Cl | H | 255-257° C. (hydrochloride) optical rotation: +26.8° (c = 1; water, 22° C., 589 nm) |
| 57 Stereoisomer-3 | Me | o-Cl | H | 229-230° C. (hydrochloride) optical rotation: +8.9° (c = 1; water, 20° C., 589 nm) |
| 58 Stereoisomer-4 | Me | o-Cl | H | 257–258° C. (hydrochloride) optical rotation: −30.9° (c = 1; water, 22° C., 589 nm) |
| 59 Stereoisomer-1 | Me | o-F | H | 83–84° C. (succinate) optical rotation: +15.4° (c = 1; water, 20° C., 589 nm) |
| 60 Stereoisomer-2 | Me | o-F | H | 146–147° C. (succinate) optical rotation: +2.5° (c = 1; water, 20° C., 589 nm) |
| 61 Stereoisomer-3 | Me | o-F | H | 83–84° C. (succinate) optical rotation: +14.6° (c = 1; water, 20° C., 589 nm) |
| 62 Stereoisomer-4 | Me | o-F | H | 136–137° C. (succinate) optical rotation: −4.8° (c = 1; water, 20° C., 589 nm) |

Me = Methyl
* IS: Carbonyl absorption at 1695 cm$^{-1}$
** IS: Carbonyl absorption at 1712 cm$^{-1}$

EXAMPLE 63

(1-Aza-bicyclo[2.2.2]oct-3-yl)-carbamic acid benzo[1,3]dioxol-5-ylmethyl ester

Prepared in analogy to example 1, 2 or 5.
Mp (hydrochloride)=186–187° C.

EXAMPLE 64

(1-Aza-bicyclo[2.2.2]oct-3-yl)-carbamic acid benzo[1,3]dioxol-4-nitro-5-ylmethyl ester Prepared in analogy to example 1, 2 or 5.
Mp (hydrochloride)=216–218° C.

EXAMPLE 65

(1-Aza-bicyclo[2.2.2]oct-3-yl)-carbamic acid 3,4,5-trimethoxy-benzyl ester

Prepared in analogy to example 1, 2 or 5.
Mp (hydrochloride)=211–212° C.

EXAMPLE 66

1-Aza-bicyclo[2.2.2]oct-3-yl)-carbamic acid benzo[1,2,5]thiadiazol-5-ylmethyl ester Prepared in analogy to example 1, 2 or 5.
IS: Carbonyl absorption at 1718 cm$^{-1}$

What is claimed is:
1. A compound of formula I

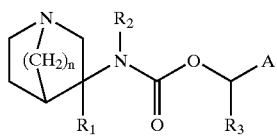

I wherein
n is 1 or 2;
$R_1$, $R_2$ and $R_3$, independently, are hydrogen or ($C_{1-4}$alkyl; and
A is selected from the group consisting of formulae

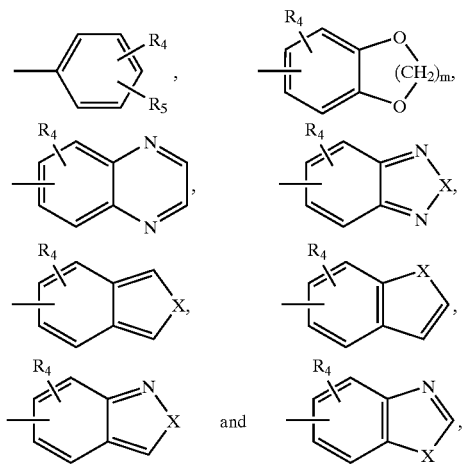

wherein
m is 1, 2 or 3;
X is O, S, NH or $CH_2$; and
$R_4$ and $R_5$, independently, are hydrogen, halogen, hydroxy, ($C_{1-4}$)alkyl, ($C_{1-4}$)alkoxy, ($C_{1-4}$)alkylthio, ($C_{1-4}$)alkylamino, nitro, trifluoromethyl or phenyl; in free base or acid addition salt form.

2. A compound according to claim 1 which is a stereoisomer of the (1-azabicyclo[2.2.2]oct-3-yl)carbamic acid 1-(2-fluorophenyl)-ethyl ester, in free base or acid addition salt form.

3. A compound according to claim 1 which is a stereoisomer of the (1-azabicyclo[2.2.2]oct-3-yl)carbamic acid 1-(2-fluorophenyl)-ethyl ester, the succinate of which has a melting point of 83–840° C., in free base or acid addition salt form.

4. A compound according to claim 1 which is a stereoisomer of the (1-azabicyclo[2.2.2]oct-3-yl)carbamic acid 1-(2-fiuorophenyl)-ethyl ester, the succinate of which has a melting point of 83–84° C. and which has an optical rotation of +14.60 ° (c=1; water, 20° C., 589 nM), in free base or acid addition salt form.

5. A process for the preparation of a compound of formula I as defined in claim 1, or a salt thereof, which comprises the step of reacting a compound of formula II

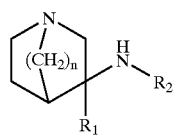

II wherein n, $R_1$ and $R_2$ are as defined in claim 11, with a compound of formula II

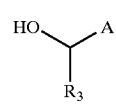

III wherein
$R_3$ and A are as defined in claim 11; and
N,N'-carbonyldiimidazole or di(N-succinimidyl) carbonate, and recovering the resulting compound of formula I in free base or acid addition salt form.

6. A process for the preparation of a compound of formula I as defined in claim 1, a salt thereof, which comprises the step of reacting a compound of formula II

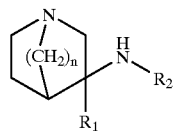

II wherein n, $R_1$ and $R_2$ are as defined in claim 1, with a compound of formula IV

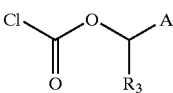

IV wherein $R_3$ and A are as defined in claim 1, and recovering the resulting compound of formula I in free base or acid additional salt form.

7. A method for the treatment of psychotic and neurodegenerative disorders, in a subject in need of such treatment, which comprises administering to such subject a therapeutically effective amount of a compound of claim 1 in free base or pharmaceutically acceptable acid addition salt form.

8. A pharmaceutical composition comprising a pharmaceutically acceptable carrier or diluent and a therapeutically effective amount of a compound of claim 1, in free base or pharmaceutically acceptable acid addition salt form.

* * * * *